United States Patent [19]
Shaw

[11] Patent Number: 5,817,058
[45] Date of Patent: Oct. 6, 1998

[54] RETRACTABLE CATHETER INTRODUCER STRUCTURE

[76] Inventor: Thomas J. Shaw, 1510 Hillcrest, Little Elm, Tex. 75068

[21] Appl. No.: 773,211

[22] Filed: Dec. 23, 1996

[51] Int. Cl.$^6$ ............................. A61M 5/178; A61M 5/50
[52] U.S. Cl. ......................... 604/110; 604/164; 604/195; 604/198
[58] Field of Search ................................ 604/110, 195, 604/187, 198, 263, 164, 168

[56] References Cited

U.S. PATENT DOCUMENTS

| | | |
|---|---|---|
| 4,747,831 | 5/1988 | Kulli . |
| 4,828,548 | 5/1989 | Walter . |
| 4,994,034 | 2/1991 | Botich et al. ............................ 604/110 |
| 5,019,044 | 5/1991 | Tsao ........................................ 604/110 |
| 5,024,665 | 6/1991 | Kaufman . |
| 5,114,410 | 5/1992 | Caralt Batlle ........................... 604/195 |
| 5,129,884 | 7/1992 | Dysarz . |
| 5,207,647 | 5/1993 | Phelps . |
| 5,267,961 | 12/1993 | Shaw . |
| 5,385,551 | 1/1995 | Shaw . |
| 5,389,076 | 2/1995 | Shaw . |
| 5,407,431 | 4/1995 | Botich et al. . |
| 5,407,436 | 4/1995 | Toft et al. ............................... 604/195 |
| 5,423,758 | 6/1995 | Shaw . |
| 5,501,675 | 3/1996 | Erskine . |
| 5,573,510 | 11/1996 | Isaacson ............................. 604/164 X |
| 5,575,777 | 11/1996 | Cover et al. ........................ 604/168 X |
| 5,578,011 | 11/1996 | Shaw . |
| 5,613,952 | 3/1997 | Pressly, Sr. et al. ..................... 604/110 |

*Primary Examiner*—Danton D. DeMille
*Assistant Examiner*—Luke Yeh

[57] ABSTRACT

A retractable catheter introducer structure includes a stepped housing and a retractable needle holder. The head of the needle holder is held in a first embodiment by means of a plunger tube having a landed front opening and in a second embodiment wherein the head of the needle holder is possessed of a surrounding ring member which can be pressed upon and released by the open mouth of an elongated tube. A catheter needle extends from the front of the housing to which a catheter assembly is removably attached. Both embodiments provide one handed operation. Retraction is triggered by pulling on the housing with the plunger tube backed against the palm of the hand to release the needle holder. Until the introducer structure is separated, the catheter assembly remains attached to the housing after retraction is triggered giving the operator greater control by reducing uncontrolled fluid egress.

36 Claims, 3 Drawing Sheets

Fig. 6

Fig. 7

RETRACTABLE CATHETER INTRODUCER STRUCTURE

FIELD OF THE INVENTION

The invention is a medical device designed to facilitate insertion of a catheter into a patient's body.

BACKGROUND OF THE PRIOR ART

Catheter insertion devices are well known in the art. When a catheter is inserted into a patient for the intravenous delivery of a fluid, a disposable needle passing through the catheter is utilized to make a puncture to permit entry of the tip of the catheter into the patient. The needle is then withdrawn leaving the catheter in place either for a direct hook up to a bottle of fluid to be delivered, or to be capped for later use. The needle which is now contaminated with blood or other body fluid must be disposed of without creating a risk of needle sticks to medical personnel which are engaged in the operation of inserting a catheter. A danger to clean up and medical waste disposal personnel continues if the used needles are not rendered harmless in some way. Caps or covers that can be mounted over the needle are not a satisfactory solution because they must be put in place and can come loose and expose the used needle. An excellent discussion of the problems associated with various approaches and uses of cannula insertion products is found in Kulli, U.S. Pat. No. 4,747,831 which is incorporated herein by reference.

Retractable needles have been recognized as the best solution of these problems. A number of these approaches are disclosed in U.S. Pat. No. 4,747,831, mentioned above, which includes an external latch mechanism which is pushed to release a spring loaded needle which is withdrawn into the chamber of the device. Some embodiments have a sliding block and retractable fingers which depress spring loaded ears to allow retraction of the needle holder, racheting devices which unlatch the needle holder by rotation of parts and even frangible parts which are broken when a plunger is pushed forward. Dysarz, U.S. Pat. No. 5,129,884 is another example of an external latch which may be disengaged to allow a needle holder to withdraw a needle into the main body of the device. Walter, U.S. Pat. No. 4,828,548 discloses a holder having a piston which may be operated on by vacuum to withdraw a needle. Erskine, U.S. Pat. No. 5,501,675 is a more recent version of a latch operated device wherein a needle holding part may be released with an external latch.

The devices of the prior art often have too many complicated parts which are difficult to manufacture and especially difficult to assemble in a high speed manufacturing operation. Many of them are prone to premature firing during handling and some are difficult to know when the needle is safe. Desirable one handed operation is either not achieved or not easy to accomplish in the emergency room environment. Disengagement of the catheter assembly from the retraction device is not fully under the timing and control of the medical operator because retraction results in immediate separation of the device from the cannula. The device of the invention solves these and other problems.

SUMMARY OF THE INVENTION

The retractable catheter introducer structure has a simple streamlined shape with a retraction mechanism which is simpler to operate, less prone to premature retraction and more reliable than other prior art catheter introducer devices. The device can be operated with one hand in any rotated position with respect to the hand because it has no external latches which require placing the device in a particular orientation. With the device held in the hand, the retraction force is applied linearly along the main longitudinal axis by the normal motion of pulling the housing straight back with the fingers. A very short stroke movement is sufficient to trigger retraction. Successful retraction is noted both visually and audibly because the medical technician can see the retracted parts in the housing and retraction creates an unobtrusive noise.

The front of the housing is made to receive a standard catheter hub which is not connected in any way to the retractable parts and does not automatically disengage from the introducer housing when retraction occurs. Disengagement of the catheter assembly from the retraction device is fully under the control of the medical operator who can separate and safely drop the introducer device while simultaneously connecting a proximately located tube connector to the catheter hub thereby minimizing egress of the patient's fluid. The number of parts are few. The parts are designed for high speed, mass production and mechanized assembly at the lowest cost.

The invention is illustrated in two preferred embodiments. One embodiment includes a retractable needle holder having an elongated body with a head larger than the body. The landed front opening of a plunger tube releasably grips the head concentrically in longitudinal axial alignment with the needle holder in an elongated preferably stepped housing. The elongated housing has a spring chamber in front and a tube chamber behind the spring chamber with an open back end. The needle holder is held in the landed front opening and provided with a spring. The combined parts are pushed forwardly into the housing with a portion of the spring and needle holder grounded in the spring chamber in the front portion of the housing. The outwardly facing surface of the landed opening is in frictional engagement with the internal wall of the housing and held in place with the needle extended for use in opposition to the retraction force applied to the needle holder by the spring. A "flash" or "flashing" chamber is carried by the head of the needle holder while extending the back into a retraction cavity formed within the plunger tube. Retraction smoothly occurs by drawing the housing back in relation to the plunger tube thereby pushing the landed opening forward and away from the head of the needle holder whereby the released needle holder is retracted into the plunger tube and housing by a force provided by the spring.

In a second embodiment, a removable ring member surrounds the head of the needle holder. The ring member has an outer surface which frictionally engages the inner wall surface of a housing. A flash chamber may be carried by the housing as in the first embodiment. A tube having walls that define an open mouth rests against the ring member after the combined needle holder and ring member are slid into the forward portion of the housing with the spring compressed and the catheter needle extended in the use position. When the housing is pulled back, the tube member pushes the ring member from the head of the housing freeing the needle holder which is then retracted under influence of the spring into a retraction cavity in the tube while the needle is drawn into the housing. Either embodiment may have a small constriction or a plurality of small inwardly pointing projections which are positioned to be just behind the ring member or landed front opening with the structure is assembled in a position for use. This may provide additional resistance to rearward movement and reduce the amount of frictional holding force required to resist the spring and any expected force on the needle arising from insertion procedures.

A method of assembling each of the preferred embodiments is disclosed which requires only axial longitudinal movement of the retraction parts with respect to the housing, making the structure ideally suited for mass production.

DETAILED DESCRIPTION OF THE PREFERRED EMBODIMENT

In the description that follows, like parts will be given the same reference numerals. The drawings of the preferred embodiments are generally true to scale and the parts are circular. Like parts in the second embodiment use the same reference numerals with a prime. With the catheter introducer assembly prepared for use, a portion of the plunger tube in FIG. 1 which extends from the housing is about 3 inches long so that the back end of the tube can be nestled against the back of the palm of the hand while the fingers grip the concave housing to facilitate one handed operation. Pulling back on the fingers triggers retraction.

Figure 1:
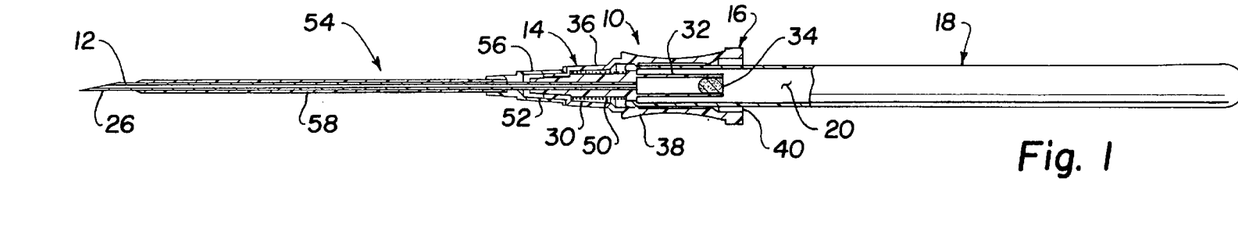
FIG. 1 is a partially cut away side or plan view of a first embodiment of a retractable catheter, cut away on the center line.
Figure 2:
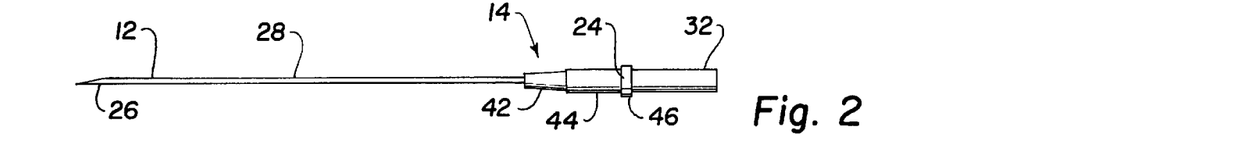
FIG. 2 shows the needle holder with a catheter needle attached thereto.

FIG. 1 shows the completed assembly 10 of the first embodiment ready for use with a catheter assembly and tube in place. Catheter introducer structure 10 has a needle 12 in a retractable needle holder 14 surrounding the back end portion of needle 12. Needle holder 14 is retractably mounted within the forward portion of a stepped housing 16 having an open back end and a concave grip 62. A plunger tube 18 having a retraction cavity 20 has a landed front opening 22 concentrically and releasably engaging the head 24 of needle holder 14. There is no requirement of a fluid tight seal between the plunger tube and the housing.

Catheter needle 12 has a point 26 in front, an intermediate portion 28 and a back end portion 30 fixedly and concentrically mounted in needle holder 14. The needle is preferably hollow having a fluid passageway in communication with a flash chamber 32 formed by a wall extending longitudinally rearwardly from head 24 of the needle holder and within the front part of plunger tube 18 when the needle holder and plunger tube are assembled. The back of the circular wall that forms flash chamber 32 is stopped with a porous plug 34 which allows air to escape when fluid is introduced.

Figure 4:
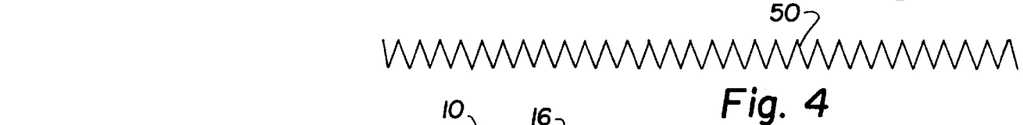
FIG. 4 illustrates the uncompressed length of a spring which is compressed under the head of the needle holder in FIGS. 1, 5, 6 and 8.

Housing 16 has a forward portion 36 and a body portion 38 extending rearwardly therefrom having an interior surface 60 preferably defining a stepped opening therethrough. The back of stepped housing 16 defines opening 40 which receives the tube 18. Retractable needle holder 14 has an elongate body comprising a front reduced diameter preferably tapered front portion 42, a radially uniform intermediate body portion 44 with head 24 behind intermediate body portion 44 being radially enlarged relative to body 44. Head 24 has a limited longitudinal extension with an outwardly facing surface 46 adapted to be releasably gripped by an inwardly facing surface 48 at landed front opening 22 of tube 18. The spring 50 of FIG. 4 is seen compressed under head 24 and bottomed in forward portion 36 of housing 16 in FIGS. 1, 5 and 6.

Figure 5:
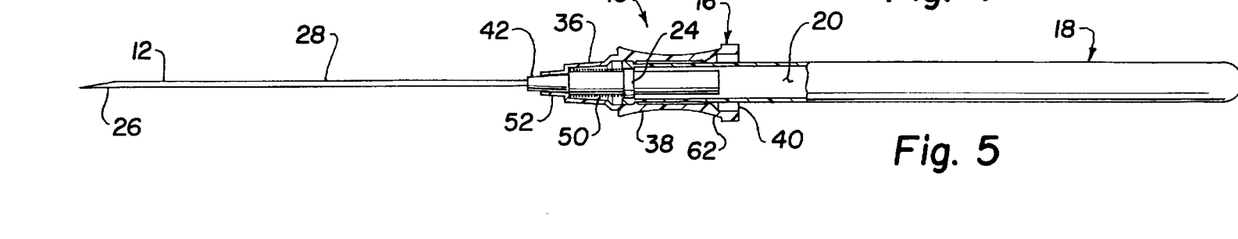
FIG. 5 is a partially cut away view of the assembled components of FIG. 3 installed for use in a stepped housing with the needle extended before the catheter assembly is attached.

In FIG. 5, a reduced diameter tip 52 is seen extending forwardly from forward portion 36 of housing 16, the tip 52 having an opening configured to receive pointed section 42 comprising the front portion of the needle holder when assembled in use position. Tip 52 is adapted to removably receive the hub 56 of the catheter assembly 54 which includes a flexible implantable catheter tube 58 which extends forwardly from hub 56 and is fixed to the hub. Tube 58 is slidably disposed over the extending part of the needle 12 when in the fully extended use position shown in FIG. 1.

Figure 6:
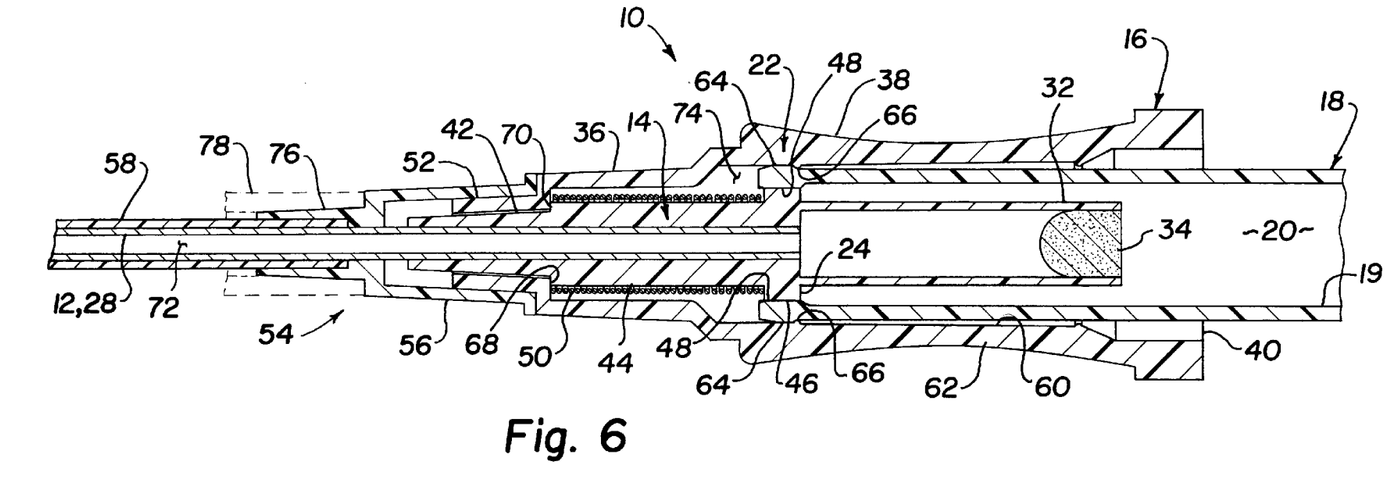
FIG. 6 is a cut away view of the assembled parts illustrated in FIG. 5 with the catheter needle extended for use and the catheter assembly removably attached to a forwardly disposed tip on the front of the housing, with the spring compressed in a ready for use position.

FIG. 6 is an enlarged sectional view of retractable catheter introducer structure 10 of FIG. 1 in use position with the needle extended and catheter assembly 54 in place. Housing 16 preferably has a stepped opening therethrough from forwardly extending tip 52, the forward portion 36 to rearwardly extending portion 38, having an internal wall surface 60. Forward portion 36 concentrically surrounds needle holder body 44 at one preferably stepped portion while body portion 38 concentrically surrounds the combined head 24 of needle holder 14 and landed front opening 22 of plunger tube 18 at another of the preferably stepped portions of the housing. Interior surface 60 of body portion 38 grippingly but slidably holds landed front opening 72 against a retraction force of spring 50 compressed under head 24 with the needle extended for use.

Plunger tube 18 has a longitudinally extending wall 19 which terminates in landed front opening 22. Landed front opening 22 has an inwardly facing surface 48 (land) which cooperates to releasably grip outwardly facing surface 46 on head 24 of the needle holder 14. Inwardly facing surface 48 has a diameter less than the diameter of cavity 20 so wall 19 won't interfere with retraction of needle holder 14. Landed head 22 is radially enlarged relative to the outer diameter of wall 19 of plunger tube 18 at a outwardly facing surface 64 (land) of limited longitudinal extension which cooperates with interior wall surface 60 of the housing to slidably hold the plunger tube in the unretracted position shown in FIG. 6. The landed head could grip the head of the needle holder by means of a plurality of separated finger portions with openings between the fingers.

Further, a small constriction 66, which may take the form of an annular ring or a plurality of individual inwardly pointing projections, is formed on and around interior wall surface 60 of body portion 38 just behind outwardly facing surface 64 of landed opening 22. Constriction 66, or a plurality thereof, serve to resist rearward movement of the plunger tube 18 and combined needle holder 14 when they are installed in the housing with the needle extended for use. The front of forward portion 36 of the housing may include a stepped abutment 68. The front of body portion 44 may have a cooperating abutment 70 whereby needle holder 14 is grounded in the forward portion of the housing. Constriction 66 is located just behind outwardly facing surface 64 of landed opening 22 when the plunger tube and grounded needle holder are installed in the housing to position the needle for use.

Needle 12, 28, 30 is preferably hollow with a fluid path 72 in communication with flash chamber 32 behind head 24 of needle holder 14. One stepped portion 36 comprising the forward portion of housing 16 constitutes a spring chamber which closely confines the front part of the spring and intermediate body portion of needle holder 14 with the needle extended for use. The internal portion of housing 16 defined by surface 60 constitutes a tube chamber radially enlarged relative to the spring chamber to slidingly receive the combined landed front opening 22 of plunger tube 18 and head 24 of needle holder 14 with the needle extended for use. The combined landed front opening 22 and head 24 are spaced behind the spring chamber a distance sufficient to allow space around intermediate body portion 44 and interior surface 60 to receive landed head 22 when it is pushed forward to release head 24 of needle holder 14 and thereby cause retraction of the needle holder into retraction cavity 20.

Catheter attachment assembly 54 is removably attached to the front of the housing. A stepped forwardly extending tip 52 of housing 16 surrounds rearwardly disposed reduced diameter pointed section 42 extending from the radially uniform intermediate body portion 44. Forwardly disposed tip 52 at the front of the housing is adapted to removably receive hub 56 with catheter tube 58 slidingly mounted on needle 12. The reduced diameter pointed section 42 is nested within the tip 52 of housing 16 and the hub 56 is nested over that combination. Hub 56 may have a further stepped portion 76 at the front which can removably receive a cap or closure 78 which is shown in phantom. A tapered friction fit between tip 52 and hub 56 may serve to releasably hold the catheter assembly in place. Tip 52 is configured to receive a standard hub.

Figure 7:
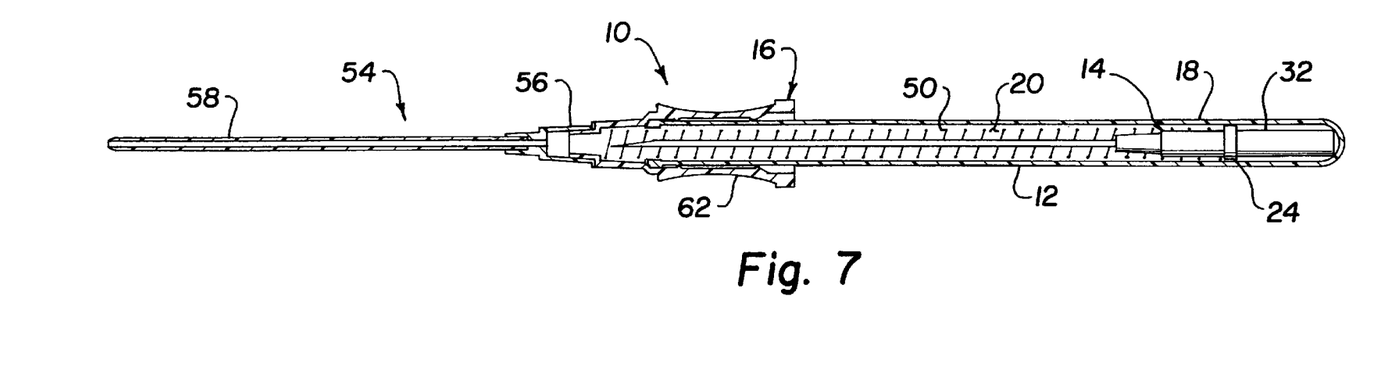
FIG. 7 shows the retracted position of the catheter assembly of FIGS. 1 through 6 with the catheter assembly still in place on the front of the housing.

FIG. 7 shows the retracted position of the catheter introducer structure of FIG. 6 before the catheter attachment assembly is removed from the front of housing 16. The needle holder and most of the needle are driven back into retraction cavity 20 and the point of the needle is withdrawn safely into the housing.

Figure 8:
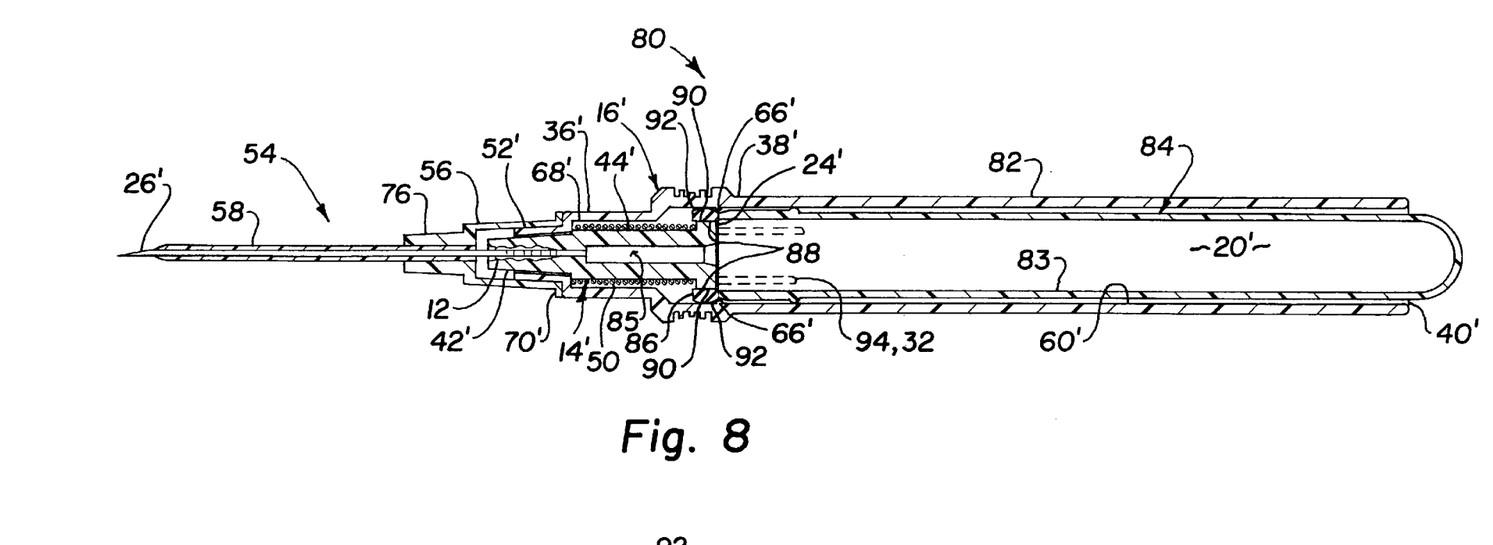
FIG. 8 is an alternate embodiment cut away on a center line with a catheter assembly attached to the front of a modified housing in a position ready for use.
Figure 9:
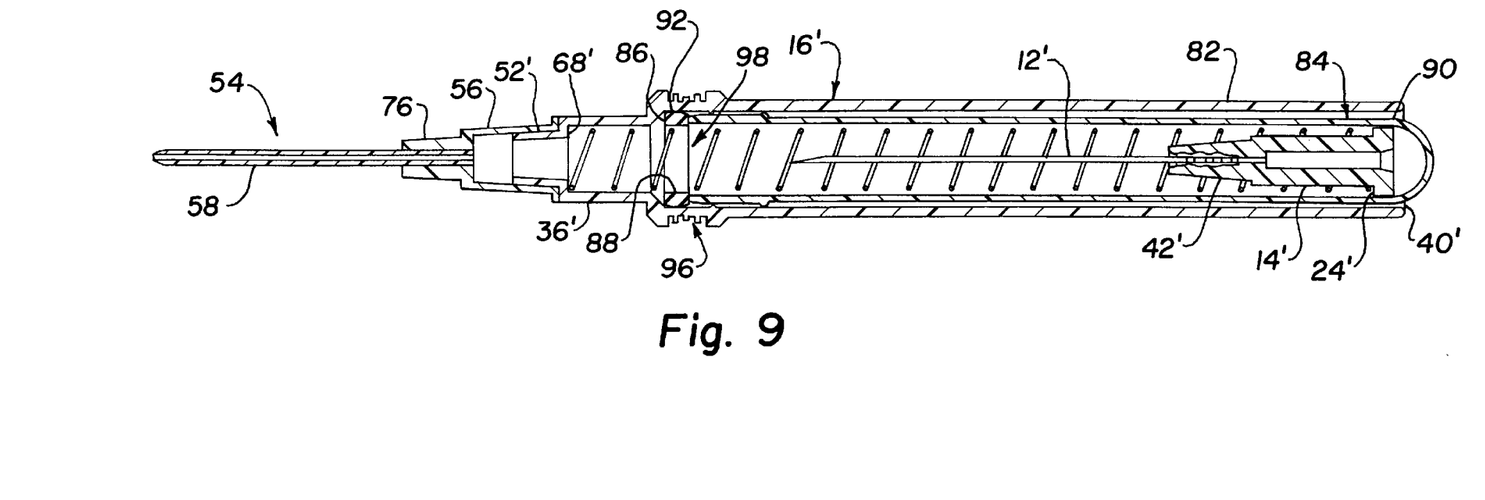
FIG. 9 shows the alternate catheter introducer structure immediately after retraction of the needle with the catheter assembly still in place.

FIGS. 8 and 9 represent a second embodiment of the invention referred to generally as catheter introducer structure 80. Catheter introducer structure 80 differs from catheter structure 10 in that housing 16' has an elongated wall 82 which extends rearwardly from a forward portion 36' comprising the spring chamber which preferably closely confines the compressed spring 50 centered around intermediate body portion 44' of needle holder 14' under head 24'. Elongated wall 82 has an interior wall surface 60' which forms a stepped opening through the housing with an opening 40' in the back of the housing to receive the retractable parts and hollow tube 84 having retraction cavity 20' therein. Tube 84 has an axially longitudinal extending wall 83 having an open mouth larger than head 24'.

Housing 16' has a preferably tapered forwardly extending tip 52', extending from forward portion 36'. Retractable needle holder 14' surrounds the back end portion of needle 12' which in this case is shown with irregular glue openings around the needle and a tubular passage 85 in fluid communication with the needle. Needle holder 14' has an elongate body comprising a preferably tapered front portion 42', straight intermediate portion 44' and head 24' radially enlarged relative to intermediate body portion 44'. A ring member 86 is removably mounted on head 24', ring member 86 having an inwardly facing surface 88 in gripping contact with an outwardly facing surface 90 around head 24' of retractable needle holder 14'. Ring member 86 has an outwardly facing surface 92 configured to slidingly grip tubular wall surface 60' of housing 16'.

Tube 84 is not connected to ring member 86, but wall 83 with open mouth 98 in front is configured to contact the ring member 86 without also contacting head 24' of needle holder 14'. A portion 94 of the wall of a flash chamber 32 just like that shown in FIG. 6 is partially illustrated in phantom as a preferred embodiment although the preferred flash chamber 32 is not actually shown in FIGS. 8 and 9. FIG. 9 shows the retracted position of the structure of FIG. 8. If the preferred flash chamber is present, it is carried with needle holder 24' and would actually contact the back of the retraction cavity 20' like in FIG. 7 but the needle would still be retracted entirely and safely within the housing. The diameter of head 24' is preferably larger than the diameter of wall 94 thereby leaving a part of the head adjacent to wall 94 available to be operated on by a tool during installation.

With the needle extended for use in FIG. 8, a small constriction 66', which may take the form of an annular ring or a plurality of individual inwardly pointing projections, is formed on interior wall surface 60' of body portion 38' extending rearwardly and longitudinally behind front portion 36' in the form of elongated wall 82. Cooperating abutment surfaces 70' on the front of intermediate body portion 44' of needle holder 14' and abutment surface 68' on the interior of stepped front portion 36' may serve to ground needle holder 14' in the front of the housing with the needle extended in use position. Constriction 66', or a plurality thereof, are configured and located just behind outwardly facing surface 92 of ring member 86 with the needle holder grounded and the needle extended in the position of use. These constrictions are small enough to allow the combined ring member 86 and head 24' of the needle holder to pass by during installation, yet serve to resist rearward movement of the ring member, and through its grip on head 24', needle holder 14' from rearward movement resulting from retraction force applied by spring 50. Tube 84 can be removed or replaced without affecting the position of the needle holder and needle.

Catheter assembly 54 is removably attached to the front of stepped housing 16'. The stepped forwardly extending tip 52' of housing 16' surrounds forwardly disposed reduced diameter pointed section 42' from which the needle extends. Tip 52' extends over part 42' in nested fashion along with nested hub 56 of catheter 54 which is removably attached to tip 52' in a tapered nested fit. Assembly 54 may include a stepped portion 76 on hub 56 which can serve to receive a removable protective cap.

FIG. 9 shows the retracted position of the structure of FIG. 8. Preferably stepped housing 16' is seen with catheter attachment assembly 54 still in place with catheter tube 58 extended. The length of elongated portion 82 of housing 16' is such that the back end of tube 84 can be fitted against the heel of the palm and the fingers can reach grip 96 located in the vicinity of the installed unretracted needle holder. By pulling the housing back, ring member 86 is removed by wall 83 from head 24' of needle holder 14' by movement of the tube forward relative to elongated housing 16'. There is sufficient space around the body 44' of the needle holder below ring member 86 to accommodate and receive ring member 86 as it is pushed from head 24'. When ring member 86 is thus pushed forward, retraction occurs and ring member 86 remains just above the spring chamber within forward portion 36' of housing 16'. Now it is safe to remove the introducer structure with one hand while holding hub 56 of the catheter tube with the other hand.

The catheter introducer structure is well suited for automated manufacture and assembly. Aside from the catheter assembly, needle and spring, only a housing, retractable needle holder and a tube are needed. The second embodiment additionally requires a ring member for the needle holder head. Although the housing could be made with in a straight configuration with a straight internal wall, it is preferably made with a stepped configuration with tapers outwardly from front to back. This makes it easy to withdraw a mandrel used in the molding process to form the internal surfaces. The housing, needle holder and tube are preferably made from transparent or semi-transparent polymeric material to allow visual access to the flash chamber which gives positive evidence of a good insertion into the patient. The fluid flows back through the needle into the flash chamber where it is readily seen.

Assembly is simple because everything moves from back to front in linear motion. Thus it is suitable for high speed mechanization. The needle can be "insert" molded into the needle holder which would look like FIG. 6 or it can be glued into an opening which would look like FIG. 8. In the latter case, the needle can be installed either before or after installation of the needle holder into the housing.

Figure 3:
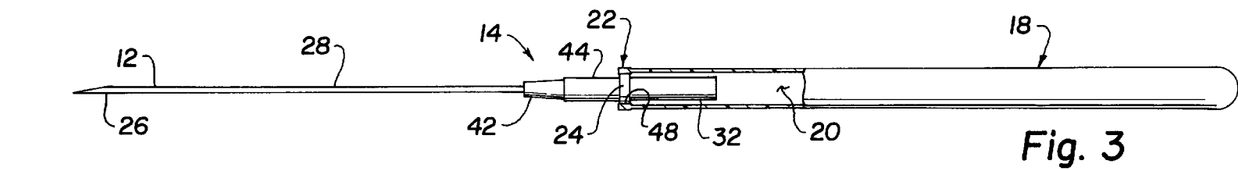
FIG. 3 illustrates the needle holder of FIG. 2 showing its head releasably mounted and held at the landed front opening of a partially cut away plunger tube.

Assembly of the first embodiment merely requires releasably mounting the head 24 of the needle holder within landed front opening 22 in the manner shown in FIG. 3. The needle holder and plunger tube are axially and longitudinally aligned and are subsequently handled as a unit. The spring can be positioned into the spring chamber with the spring circumscribing the intermediate body portion of the needle holder. The combined needle holder and plunger tube are slid into the housing to the forward position of use while compressing the spring as shown in FIG. 5. If the needle is "insert" molded, it is passed through the front opening of the housing and guided by the tapered forwardly extending pointed part 42 as the needle holder is bottomed in the front portion 36 of the housing. Alternately, the needle could be glued into a premolded opening which passes through the needle holder in the manner shown in FIG. 8 after the needle holder is installed in the housing. The close fit between the outwardly facing surface of the plunger tube in sliding but gripping contact with the internal wall surface of the housing holds the assembled plunger tube and needle holder in the use position shown in FIG. 6.

If a constriction 66 is provided on the internal wall of the housing, the step of sliding the combined needle holder and plunger tube includes the step of passing the outwardly facing surface of the plunger tube over the constriction, which serves to provide additional resistance to backward movement of the plunger tube in response to the spring force applied to the under side of the head of the needle holder and any additional insertion force that might be applied to the needle. The needle holder is preferably bottomed in the housing just as the step of passing the outwardly facing surface of the plunger tube over the constriction is completed. This step simultaneously extends the forwardly exposed reduced diameter pointed section of the needle holder in nested relation to the tip 52 which in turn is nested under the hub 56 of the catheter attachment assembly when the catheter attachment assembly is attached in FIG. 1. It is believed that one skilled in the art could easily provide fixtures for stations to provide repetitive parts, subassembly the parts and then put them together.

The assembly method for the alternate embodiment shown in FIGS. 8 and 9 is similar except that the head of the needle holder is provided with a removable ring member which circumscribes the head and has an outwardly facing surface that slidingly grips the interior wall of the housing. The ring member is first placed upon the head of the needle holder in the position shown in FIG. 8. The spring followed by the needle holder is introduced in containment within the tube chamber with the spring circumscribing the needle holder body below the head. A separate tool which fits into the housing would have a circular end which presses against the ring member and head of the needle holder and pushes them down together. If the flash chamber is present, the tool may include a central recess to receive the flash chamber and longitudinal walls which simultaneously engage the ring member and that outer portion of head 24' which extends radially beyond the outer diameter of wall 94 of a flash chamber 32.

The combined needle holder and ring are pushed into the hollow forward portion of the housing to the forward position of use while compressing the spring; the needle holder being grounded in front of the housing. The needle holder is prevented from moving in response to the compressed spring by gripping of the outer surface of the ring against the inner surface of the housing. As in the case of the first embodiment, the needle can be molded into the retraction member or glued into a prepared opening by passing the needle into the front of the needle holder after the needle holder is bottomed in the front of the housing. The front of tube 84 which is used to trigger retraction is then slid into opening 40' in the back of elongated housing 16' where it is brought up in proximity to the ring member and in contact therewith.

In operation, retraction of the first embodiment occurs after insertion of the catheter needle when the plunger tube is pushed forward relative to the housing while the needle holder remains bottomed in the housing until the head of the needle holder comes free. This allows the spring to uncoil and drive the needle holder back into the retraction chamber, pulling the needle behind and leaving the catheter tube 58 in place. The second embodiment operates in the same manner except that wall 84 that defines opening 98 of tube 84 which is in contact with ring member 86 drives the ring member forward into space in the tube chamber below the head of the needle holder thereby releasing the needle holder from the ring member. The spring then drives the needle holder into retraction cavity 20' carrying most of the needle into the retraction cavity and all of the needle safely into the housing.

An important aspect of the operation is the fact that the operator can conveniently operate the retractable introducer structure with one hand. One handed operation is possible in that the tube 18, 84, is about 3 inches longer than the handle grip part 62, 96 of the device to allow backing the tube against the fleshy part of the palm while employing the fingers to pull the housing back to smoothly initiate retraction. The other hand is free to grasp the catheter hub. Timing for freeing the hub from the introducer device and attaching an IV tube to the catheter hub is under complete control of the medical technician. The operator can hold the introducer device in one hand, reach for the IV tube connector with the other hand and bring them all close together with the introducer structure cupped in the palm of the hand. Some of the fingers can reach the grip while the thumb and forefinger can grasp the IV connector. Upon successful insertion of the needle and the catheter tube, the operator can pull the fingers back to immediately retract the needle. In one motion the hub of the catheter can be separated from the insertion device which is dropped while the connection is then made to the IV tube or other device which is to be connected to the patient. The catheter introducer device can be dropped without concern because the needle has already been safely retracted before the catheter assembly was disconnected from the housing. When the fingers pull back on the housing to trigger retraction, the operator can both hear and see that the needle is safely retracted and immediately drop the device to free his hand for use in making the necessary connection before loss of fluid from the patient occurs.

The catheter introducer does not have to resist much force imposed by the needle on the retraction parts as does a conventional syringe which is required to puncture a rubber seal commonly used on vials. Consequently, the retractable parts need only be able to resist about 3 pounds of force or less without retracting. Frictional force between the landed opening or the ring member and the internal wall of the housing should be able to withstand a force tending to cause retraction of that amount. Best seen in FIG. 6 and equally applicable to the ring member of FIGS. 8 and 9, the outer surface 64 of the landed opening or surface 92 of the ring member is preferably curved when seen in cross section and may have a short flat spot in contact with the wall. This facilitates sliding movement and can help control the amount of sliding frictional resistance resulting from part tolerance variations.

Concentration of radial force in a smaller area tends to increase distortion and reduce friction, particularly when using a ring member made of a polymeric material with more flexibility than the housing which may be made with moldable polypropylene. The ring member may be made of thermoplastic rubber designated 181 - 55 available from Advanced Elastomer Systems, St. Louis, Mo. and sold under the Santoprene® brand. It is said to have a hardness around 55 on the Shore A durometer scale. The needle holder may be made of polycarbonate type polymeric material. About 1 pound of the approximately 3 pounds of resistance to retraction may be provided by the small constriction 66, 66'. The head of the needle holder should be sufficiently smaller in diameter than the diameter of the retraction cavity so that air compressed behind the head does not unduly interfere with retraction.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

I claim:

1. A method of assembling a catheter introducer structure comprising the steps of:
   a. providing a retractable needle holder having an elongate body comprising a front portion, an intermediate portion and a head behind the intermediate portion, said head being radially enlarged relative to the intermediate body portion and having an outwardly facing surface;
   b. providing a plunger tube having an elongated longitudinally extending wall which forms an internal retraction cavity, the wall forming a landed front opening having an inwardly facing surface configured to releaseably hold said outwardly facing surface of the head of the needle holder, said landed front opening further including an outwardly facing surface of limited longitudinal extension for slideably engaging an interior wall surface of a housing;
   c. providing an elongated housing having a front and a hollow forward portion adapted to receive the elongate body of the needle holder and a spring mounted on the elongate body under said head, said elongated housing having a longitudinally extending wall extending rearwardly from said forward portion and forming a tubular interior wall surface defining an open ended tubular cavity within;
   d. releaseably mounting the head of the needle holder within said landed front opening;
   e. positioning the spring in containment within said forward portion circumscribing the intermediate body portion of the needle holder; and
   f. sliding the combined needle holder and plunger tube into the housing to a forward position of use while compressing the spring.

2. The assembly method of claim 1 further including the step of:
   g. mounting a needle into the needle holder in fluid communication with the plunger tube.

3. The assembly method of claim 1 wherein the step of providing a retractable needle holder includes the step of providing a catheter needle extending from the front of the needle holder and the step of sliding the combined needle holder and plunger into the housing includes the step of extending the needle from the front of the housing.

4. The assembly method of claim 1 wherein the step of providing a housing includes the step of providing a constriction in the tubular internal wall surface and the step of sliding the combined needle holder and plunger tube includes the step of passing the outwardly facing surface of the plunger tube over the constriction.

5. The assembly method of claim 4 wherein the front of the needle holder is bottomed in the housing just as the step of passing the outwardly facing surface of the plunger tube over the constriction is completed.

6. The assembly method of claim 5 wherein the step of providing a needle holder includes the step providing a forwardly disposed reduced diameter pointed section, the step of providing a housing includes the step of providing a forwardly extending tip with an opening configured to receive the pointed section and the step of sliding the needle holder into the housing includes the step of positioning said pointed section into said opening.

7. The assembly method of claim 6 wherein said forwardly extending tip is provided with an outer surface configured to removably receive the hub of a catheter assembly further including the step of mounting the hub of a catheter assembly thereon.

8. The assembly method of claim 7 further including the step of installing a catheter needle extending forwardly from said pointed section before said step of mounting the hub of a catheter assembly thereon.

9. A method of assembling a catheter introducer structure comprising the steps of:
   a. providing a retractable needle holder having an elongate body in front and a head in back, said head being radially enlarged relative to the body and having an outwardly facing surface, said head further having a flash chamber wherein said flash chamber is attached to and extends rearwardly from the head of the needle holder;

b. providing a spring mountable around said body under said head;

c. providing a ring member having an inwardly facing surface mountable on the head with the inwardly facing surface in releasable gripping contact with the outwardly facing surface of the head, the ring member having an outwardly facing surface configured to slidingly grip a tubular wall surface;

d. providing an elongated housing having a front and a hollow forward portion comprising a spring chamber to receive a spring and the elongated body portion of the needle holder, said housing having a longitudinally extending wall extending rearwardly from said forward portion comprising an interior wall surface forming a tube chamber having an open ended tubular cavity within;

e. providing a tube having a retraction cavity within and being mountable for movement within said tube chamber, said tube having an open mouth configured to contact the ring member and push it off the head;

f. releasably mounting the ring member in place upon the head of the needle holder;

g. introducing the spring followed by the needle holder into containment within the tube chamber with the spring circumscribing the needle holder body below the head;

h. pushing the combined needle holder and ring into the hollow forward portion of the housing to a forward position of use while compressing the spring wherein the outwardly facing surface of the ring member in slidable gripping contact with the tubular wall surface inside the tube chamber holds the needle holder in place with the needle extended from the housing in a position for use and;

positioning the tube in the housing with at least part of said flash chamber within said tube.

10. The assembly method of claim 9 further including the step of:

providing a catheter needle having a rear end portion and mounting said rear end portion into the front of the needle holder with the needle extending therefrom;

11. The assembly method of claim 9 wherein the step of providing a housing includes the step of providing a constriction in the tubular internal wall surface and the step of pushing the combined needle holder and ring includes the step of passing the outwardly facing surface of the ring member over the constriction.

12. The assembly method of claim 11 wherein the front of the needle holder is bottomed in the housing just as the step of passing the outwardly facing surface of the ring member over the constriction is completed.

13. The assembly method of claim 12 wherein the step of providing a needle holder includes the step providing a forwardly disposed reduced diameter pointed section, the step of providing a housing includes the step of providing a forwardly extending tip with an opening configured to receive the pointed section and the step of pushing the needle holder and ring into the housing includes the step of positioning said pointed section into said opening.

14. The assembly method of claim 13 wherein said forwardly extending tip is provided with an outer surface configured to removably receive the hub of a catheter assembly further including the step of removably mounting the hub of a catheter assembly thereon.

15. A catheter introducer structure comprising:

an elongate catheter needle having a point in front and a back end portion;

a retractable needle holder surrounding the back end portion of the needle, the needle holder having an elongate body in front and a head in back, said head being radially enlarged relative to the body and having an outwardly facing surface;

said head further including a flash chamber in fluid communication with the needle, said flash chamber being attached to and extending rearwardly from the head of the needle holder;

a spring mounted on said elongate body under said head;

a ring member removably fixed on the head, the ring member having an inwardly facing surface in gripping contact with the outwardly facing surface of the head and an outwardly facing surface configured to slidingly grip a tubular wall surface;

an elongated housing having a front and a hollow forward portion adapted to receive the elongate body of the needle holder with the needle extended through said front and said needle holder grounded in the front portion of the housing against forward movement relative to the housing;

said elongated housing having a longitudinally extending wall extending rearwardly from said forward portion and forming a tubular wall surface and an open ended tubular cavity within;

the outwardly facing surface of the ring member slideably gripping the tubular wall surface within the housing with the needle holder and compressed spring positioned within said front portion of the housing and the needle extended from the front of the housing for use;

a tube forming a retraction chamber within, the tube being mounted for reciprocation within the tubular cavity of the housing, the tube having an open mouth in front which is configured to push the ring member from the needle holder without driving the needle forward;

a catheter attachment assembly mounted on the forward portion of the housing with a catheter tube slidingly mounted on the needle; and whereby the ring member is removed off the head of the needle holder by a forward push on the tube relative to the elongated housing wherein the needle holder is retracted into the tube in response to a spring force and the needle is drawn into the housing to prevent needle sticks after use.

16. The catheter introducer structure of claim 15 wherein a constriction is formed on the interior wall surface of the housing positioned just behind the ring member when the needle holder is installed within the front portion of the housing with the needle extended from the front of the housing for use, the constriction being sufficiently small to allow the combined ring member and head of the needle holder to pass by during installation yet serving to resist rearward movement of the ring member after installation of the needle holder.

17. The catheter introducer structure of claim 14 wherein the interior of the forward portion of the housing has an abutment surface which is engaged by the front of the needle holder, the constriction being spaced behind the abutment surface at a distance such that the needle holder is grounded in the forward portion of the housing with the constriction just behind the ring member when the needle holder is installed in the housing with the needle extended for use.

18. The catheter introducer structure of claim 17 wherein the elongate body of the needle holder has a radially uniform portion below the head for centering the spring and a forwardly disposed reduced diameter pointed section from which the needle extends.

19. The catheter introducer structure of claim 18 wherein the front of the housing has a forwardly disposed tip whereby the reduced diameter section of the needle holder, said tip and a portion of the catheter attachment assembly are nested when the catheter structure is assembled with the needle extended for use.

20. The catheter introducer structure of claim 19 further including a flash chamber in fluid communication with the needle, the flash chamber being attached to and extending rearwardly from the head of the needle holder, the retraction cavity of the tube having sufficient length to receive the flash chamber, the needle holder and most of the needle.

21. A catheter introducer structure comprising:
  a needle having a point in front, a back end portion and an intermediate portion therebetween;
  a retractable needle holder surrounding the back end portion of the needle, the needle holder having an elongate body comprising a front portion, an intermediate body portion and a head behind the intermediate portion, said head being radially enlarged relative to the intermediate body portion;
  a plunger tube having a hollow body with a landed front opening concentrically and releaseably engaging the head of the needle holder in alignment therewith;
  a housing having a forward portion and a body portion extending rearwardly therefrom with an interior wall surface defining a stepped opening therethrough;
  said housing forward portion concentrically surrounding said needle holder body at one stepped portion of the stepped opening while said body portion concentrically surrounds the combined head of the needle holder and said landed front opening of the plunger tube at another stepped portion, said body portion frictionally holding said landed front opening at the interior wall against a retraction force of a spring compressed under the head of the needle holder, with the needle extended for use; and
  wherein said needle holder is released from the landed opening by sliding the plunger tube forward relative to the needle holder within said another stepped portion whereby the landed opening is disengaged from the head of the needle holder which is retracted into the plunger tube while the needle is withdrawn into the housing thereby preventing needle sticks after use.

22. The catheter introducer structure of claim 21 wherein the plunger has an elongated longitudinally extending wall which forms an internal retraction cavity, the wall terminating in said landed front opening.

23. The catheter introducer structure of claim 22 wherein the head of the needle holder has an outwardly facing surface and the landed front opening of the plunger has an inwardly facing surface which cooperate to releaseably hold the needle holder with the needle extended for use.

24. The catheter introducer structure of claim 23 wherein the landed front opening is radially enlarged relative to the plunger tube body, having an outwardly facing surface of limited longitudinal extension which cooperates with the interior wall surface of the housing to slidably hold the plunger tube when the plunger tube and needle holder are installed in the housing wit the needle extended for use.

25. The catheter introducer structure of claim 24 wherein a constriction is formed on the interior wall surface of the body portion of the housing which serves to resist rearward movement of the plunger tube when the plunger tube and needle holder are installed in the housing with the needle extended for use.

26. The catheter introducer structure of claim 25 wherein said needle holder is grounded in the forward portion of the housing and said constriction is located just behind the outwardly facing surface of the landed opening when the plunger tube and needle holder are installed in the housing to position the needle for use.

27. The catheter introducer structure of claim 26 further including a chamber in fluid communication with the needle, the chamber extending longitudinally rearwardly from the head of the needle holder within the plunger tube, said chamber being carried with the needle holder when it retracts.

28. The catheter introducer structure of claim 27 further including a catheter attachment assembly mounted on the forward portion of the housing with a catheter tube slideably mounted on the needle.

29. The catheter introducer structure of claim 26 wherein the outwardly facing surface of the needle holder generally coextensively engages the inwardly facing surface of the plunger tube along a path parallel to the longitudinal direction while the outwardly facing surface of the plunger tube has a rounded shape with a flat spot that meets the interior wall of the housing, said flat spot serving to control sliding frictional engagement with said wall surface, the length of said flat spot being less than the length of said path.

30. The catheter introducer structure of claim 21 wherein said one stepped portion of the stepped opening comprises a spring chamber which closely confines the front part of the spring and intermediate body portion of the needle holder with the needle extended for use.

31. The catheter introducer structure of claim 30 wherein said another portion of the stepped opening comprises a tube chamber behind a spring chamber, the tube chamber being enlarged radially relative to the spring chamber to slidingly receive the combined landed front opening of the plunger tube and head of the needle holder, with the needle extended for use, the head of the needle holder and landed front opening being spaced behind the spring chamber a distance that allows sufficient space between the intermediate body portion of the needle holder and the interior wall of the tube chamber below said head to receive the landed front opening part of the plunger when it is pushed forward to release the head of the needle holder and thereby cause retraction.

32. The catheter introducer structure of claim 31 wherein a constriction is formed on the interior wall surface of the housing positioned just behind the landed front opening of the plunger tube when the needle holder is installed within the front portion of the housing with the needle extended from the front of the housing for use, the constriction being sufficiently small to allow the combined front of the plunger tube and head of the needle holder to pass by during installation yet serving to resist rearward movement of the plunger after retraction of the needle holder.

33. The catheter introducer structure of claim 32 further including a flash chamber in fluid communication with the needle, said chamber extending longitudinally rearwardly from the head of the needle holder within the plunger tube, and being stopped with a porous plug to allow displaced air to escape, said chamber being carried with the needle holder when it retracts.

34. The catheter introducer structure of claim 33 further including a catheter attachment assembly mounted on the forward portion of the housing with a catheter tube slideably mounted on the needle.

35. The catheter introducer structure of claim 34 wherein the elongate body of the needle holder has a radially uniform portion below the head for centering the spring and a forwardly disposed reduced diameter pointed section from which the needle extends.

36. The catheter introducer structure of claim 35 wherein the front of the housing has a forwardly disposed tip whereby the reduced diameter section of the needle holder, said tip and a portion of the catheter attachment assembly are nested when the catheter structure is assembled with the needle extended for use.

* * * * *